US00PP33179P2

(12) United States Plant Patent
Hochberg

(10) Patent No.: US PP33,179 P2
(45) Date of Patent: Jun. 22, 2021

(54) ***LAGERSTROEMIA* PLANT NAMED 'HOCH1099'**

(50) Latin Name: *Lagerstroemia indica*
Varietal Denomination: HOCH1099

(71) Applicant: Hochberg Ornamental Export Plants Ltd, Moshav Bitzaron (IL)

(72) Inventor: Omer Hochberg, Moshav Bitzaron (IL)

(73) Assignee: Hochberg Ornamental Export Plants Ltd

( * ) Notice: Subject to any disclaimer, the term of this patent is extended or adjusted under 35 U.S.C. 154(b) by 0 days.

(21) Appl. No.: 17/094,165

(22) Filed: Nov. 10, 2020

(51) Int. Cl.
*A01H 5/02* (2018.01)
*A01H 6/00* (2018.01)

(52) U.S. Cl.
USPC ..... Plt./252
CPC ..... *A01H 6/00* (2018.05)

(58) Field of Classification Search
USPC ..... Plt./252
CPC ..... A01H 6/00
See application file for complete search history.

*Primary Examiner* — Anne Marie Grunberg
(74) *Attorney, Agent, or Firm* — Cassandra Bright

(57) ABSTRACT

A new and distinct cultivar of *Lagerstroemia* plant named 'HOCH1099' is disclosed, characterized by red-purple flowers, and green foliage. Plants are shrubby and well-branched. The new variety is a *Lagerstroemia*, normally used for outdoor ornamental purposes.

1 Drawing Sheet

Latin name of the genus and species: *Lagerstroemia indica.*

Variety denomination: 'HOCH1099'.

BACKGROUND OF THE INVENTION

The new *Lagerstroemia* cultivar is a product of a planned breeding program conducted by the inventor, in Moshav Bitzaron, Israel. The objective of the breeding program was to develop new Crepe Myrtle plants for ornamental purposes. The open-pollination resulting in this new variety was made during July of 2015.

The seed parent is the unpatented proprietary variety referred to as *Lagerstroemia* 'L103'. The pollen parent unidentified. The new variety was selected in August of 2016 by the inventor in a group of seedlings resulting from the 2014 open-pollination, in a nursery in Moshav Bitzaron, Israel. Date of first sale was Jan. 1, 2020, occurring in Europe. This sale was made directly by the inventor or one who obtained the claimed invention directly or indirectly from the inventor. This sale and all public disclosures made between Jan. 1, 2020 and the filing of this application fall within the exception allowed under 102(b)(1).

Asexual reproduction of the new cultivar was performed by softwood cuttings. This was first performed at the same nursery in Moshav Bitzaron, Israel during June of 2017, and has shown that the unique features of this cultivar are stable and reproduced true to type in multiple successive generations.

SUMMARY OF THE INVENTION

The cultivar 'HOCH1099' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'HOCH1099' These characteristics in combination distinguish 'HOCH1099' as a new and distinct *Lagerstroemia* cultivar:

1. Red-Purple blooms near 67D.
2. Green foliage near 136C.
3. Bushy plant habit, reaching 60 to 80 cm in the second year.

PARENT COMPARISON

Plants of the new cultivar 'HOCH1099' are similar to plants of the seed parent in most horticultural characteristics; however, plants of the new cultivar 'HOCH1099' differ in the following;

1. The new variety has red-purple flowers, while the seed parent has purple flowers.

The pollen parent cannot be identified as the new variety is the result of an open-pollination.

COMMERCIAL COMPARISON

Plants of the new cultivar 'HOCH1099' are comparable to the commercial variety *Lagerstroemia* 'Purple Velvet', unpatented. The two *Lagerstroemia* varieties are similar in most horticultural characteristics, however, the new variety 'HOCH1099' differs in the following;

1. The new variety has red-purple blooms; this comparator has purple blooms.
2. The new variety has darker green leaves.

Plants of the new cultivar 'HOCH1099' are comparable to the commercial variety *Lagerstroemia* 'Rhapsody in Pink', U.S. Plant Pat. No. 16,616. The two *Lagerstroemia* varieties are similar in most horticultural characteristics; however, the new variety 'HOCH1099' differs in the following;

1. The new variety has red-purple blooms, while this comparator has pink blooms.
2. The new variety has lighter green foliage than this comparator.

BRIEF DESCRIPTION OF THE PHOTOGRAPH

The accompanying photograph illustrates a typical flowering plant of 'HOCH1099' grown outdoors in Moshav Bitzaron, Israel. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'HOCH1099' plants grown outdoors in Visalia, Calif. The growing temperature ranged from approximately 18° C. to 38° C. during the day and from approximately 5° C. to 10° C. during the night. General light conditions are normal sunlight and numerical values represent averages of typical plant types. Measurements were taken during June of 2020.

Botanical classification: *Lagerstroemia indica* 'HOCH1099'.

PROPAGATION

Type of propagation typically used: Softwood cuttings.
Time to initiate roots: 21 days at 18-27° C.
Time to produce a rooted cutting: 1-2 months at 18-27° C.
Root description: Thin fibrous, dense, moderate branching. White in color, not accurately measured with R.H.S. Chart.

PLANT

Age of plant described: About 1.5 years old from a rooted cutting.
Container size: 3 gallon container.
Growth habit: Bushy.
Plant spread: 50 cm.
Plant height: 65 cm.
Plant vigor: Good.
Length of primary lateral branches: Varies as the plant is often pruned. 16 to 36 cm on average.
Diameter of lateral branches: 4 to 6 mm.
Quantity of lateral branches: About 20 to 30.
Stem:
- *Color*.—New growth: Near RHS Greyed-Purple 187B. Old growth: Near RHS Greyed-Purple 183D.
- *Shape*.—Round.
- *Strength*.—Good.
- *Aspect angle*.—Upright.
- *Texture*.—Very slightly scaly with age.

Internode length: Average range 1.6 to 2.5 cm.
Bark peel: Not observed.

FOLIAGE

Leaf:
- *Arrangement*.—Sub-opposite.
- *Average length*.—5.5 to 6.0 cm.
- *Average width*.—3.0 to 3.5 cm.
- *Shape of blade*.—Ovate.
- *Apex*.—Acute.
- *Base*.—Obtuse.
- *Margin*.—Entire.
- *Aspect*.—Undulate.
- *Texture of top surface*.—Smooth.
- *Texture of bottom surface*.—Smooth.
- *Color*.—Young foliage upper side: Near RHS Green 136A. Young foliage under side: Near RHS Green 136A. Mature foliage upper side: Near RHS Green 136C. Mature foliage under side: Near RHS Green 136C. Venation: Type: Pinnate. Venation color upper side: Near RHS Yellow-Green N144A. Venation color under side: Near RHS Yellow-Green 153C.
- *Petiole*.—Length: 2-3 mm. Diameter: 2 mm. Texture, upper side: Smooth. Texture, under side: Smooth. Color, upper side: Near RHS Yellow-Green 153A. Color, under side: Near RHS Yellow-Green 153D, flushed Greyed-Purple 187B.

FLOWER

Natural flowering season: Summer through Fall. Begins flowering mid-June in California.
Inflorescence form: Panicles.
Flowers per inflorescence: About 40 to 70 flowers and buds.
Inflorescence size:
- *Width*.—17 cm.
- *Length*.—Average 18 cm.

Individual flowers:
- *Type*.—Rotate.
- *Shape*.—Obovate.
- *Habit*.—Whorled outward.
- *Diameter*.—3.5 cm.
- *Depth*.—1.5 cm.
- *Persistence*.—Self-cleaning.
- *Fragrance*.—Faint musty scent.

Petals:
- *Arrangement*.—Whorled.
- *Number*.—6.
- *Shape*.—Overall irregular orbicular.
- *Aspect*.—Deeply undulate.
- *Margin*.—Deeply ruffled, crenate.
- *Tip shape*.—Rounded.
- *Base shape*.—Rounded.
- *Length*.—1.0 cm, undulated, cannot unfold.
- *Width*.—2.0 cm, undulated, cannot unfold.
- *Texture*.—Upper: Glabrous. Lower: Glabrous.
- *Color*.—When opening: Upper surface: Near RHS Red-Purple 72B. Under surface: Near RHS Red-Purple 72B. Fully opened: Upper surface: Near RHS Purple N78A. Under surface: Near RHS Purple N78A.

Bud:
- *Shape*.—Sphere.
- *Length*.—7 mm.
- *Diameter*.—7 mm.
- *Color*.—Near RHS Greyed-Purple 187B, base Green 138B.

Calyx:
- *Shape*.—Fused into a conical shape.
- *Length*.—12 mm.
- *Diameter*.—10 mm.

Sepals:
- *Appearance*.—Matte.
- *Arrangement*.—Rotate, fused.
- *Shape*.—Narrowly triangular.
- *Tip shape*.—Acute.
- *Base shape*.—Obtuse.
- *Margin*.—Entire.
- *Quantity per flower*.—6.
- *Length*.—12 mm.
- *Width*.—4 mm.
- *Margin*.—Entire.
- *Texture*.—Inner: Smooth. Outer: Smooth, coriaceous.
- *Color*.—Inner: Near RHS Yellow-Green 146D flushed Greyed-Purple 185C. Outer: Near RHS Yellow-Green 146C flushed Greyed-Purple 185C. Base 186C.

Peduncle:

*Length*.—Average range 1.5 to 3.0 cm.

*Diameter*.—3 mm.

*Texture*.—Glabrous.

*Color*.—Near RHS Greyed-Purple 187B, striped Greyed-Orange N170C.

*Orientation*.—Upright.

*Strength*.—Strong.

Pedicel:

*Length*.—4 to 5 mm.

*Diameter*.—1-2 mm.

*Angle*.—About 45 degrees from attachment.

*Strength*.—Moderate.

*Texture*.—Slightly pubescent.

*Color*.—Near Greyed-Purple 183B.

REPRODUCTIVE ORGANS

Stamens:

*Number*.—About 20-30, curled and congested.

*Filament length*.—5 to 15 mm, when pulled straight.

*Filament color*.—Near White 155D.

Anthers:

*Shape*.—Ovate.

*Length*.—1 mm.

*Color*.—Yellow 2C.

*Pollen*.—Not observed.

Pistil:

*Number*.—1.

*Length*.—2.9 cm.

Stigma:

*Shape*.—Globular.

*Color*.—Near RHS Greyed-Purple N186D.

*Ovary color*.—Near RHS Yellow 2D.

OTHER CHARACTERISTICS

Fruits and seeds: Not observed to date.

Disease/pest resistance: Neither resistance nor susceptibility to normal diseases and pests of *Lagerstroemia* observed.

Temperature range: Observed to tolerate a temperature range from about −2° C. to 38° C.

What is claimed is:

1. A new and distinct cultivar of *Lagerstroemia* plant named 'HOCH1099' as herein illustrated and described.

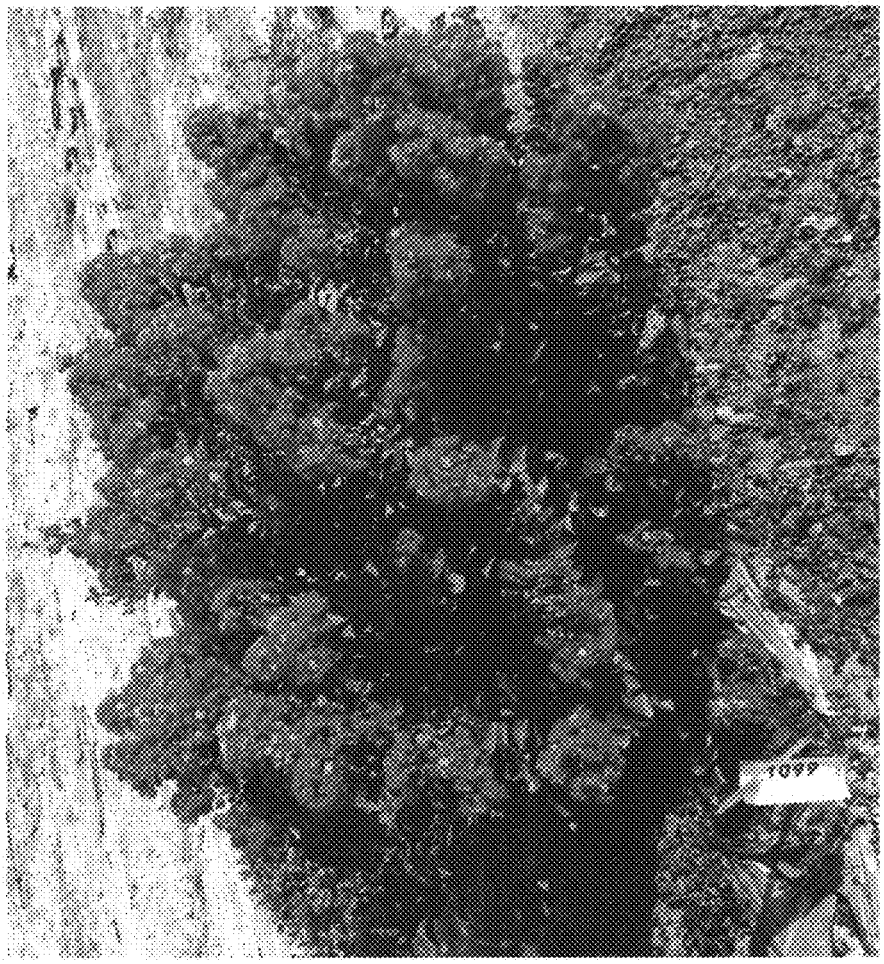

* * * * *